under 35 U.S.C. 154(b) by 51 days.

(12) United States Patent
Blick et al.

(10) Patent No.: US 10,605,800 B2
(45) Date of Patent: Mar. 31, 2020

(54) PLANAR HIGH-SPEED MOLECULE SEQUENCER

(71) Applicant: Wisconsin Alumni Research Foundation, Madison, WI (US)

(72) Inventors: Robert H. Blick, Hamburg (DE); Abhishek Bhat, Madison, WI (US); Paul Gwozdz, Hamburg (DE)

(73) Assignees: Wisconsin Alumni Research Foundation, Madison, WI (US); University of Hamburg, Hamburg (DE)

(*) Notice: Subject to any disclaimer, the term of this patent is extended or adjusted under 35 U.S.C. 154(b) by 51 days.

(21) Appl. No.: 15/926,265

(22) Filed: Mar. 20, 2018

(65) Prior Publication Data

US 2019/0293623 A1 Sep. 26, 2019

(51) Int. Cl.
*G01N 33/487* (2006.01)
*C12Q 1/6869* (2018.01)
*G01N 27/22* (2006.01)

(52) U.S. Cl.
CPC ..... *G01N 33/48721* (2013.01); *C12Q 1/6869* (2013.01); *G01N 27/221* (2013.01)

(58) Field of Classification Search
CPC . G01N 33/48721; G01N 22/00; C12Q 1/6879
See application file for complete search history.

(56) References Cited

U.S. PATENT DOCUMENTS

| | | | |
|---|---|---|---|
| 8,217,665 B2 | 7/2012 | Blick et al. | |
| 8,686,375 B2 | 4/2014 | Blick et al. | |
| 8,696,881 B2 | 4/2014 | Blick | |
| 9,086,401 B2 | 7/2015 | Blick et al. | |
| 9,322,820 B2 | 4/2016 | Blick et al. | |
| 9,329,126 B2 | 5/2016 | Blick et al. | |
| 9,488,600 B2 | 11/2016 | Blick et al. | |
| 9,575,021 B2 | 2/2017 | Blick et al. | |
| 2014/0266147 A1* | 9/2014 | Blick | G01N 33/48721 324/71.1 |
| 2015/0218630 A1* | 8/2015 | Sun | C12Q 1/6869 506/2 |
| 2019/0080760 A1* | 3/2019 | Predki | C12Q 1/68 |

* cited by examiner

*Primary Examiner* — Narayan K Bhat
(74) *Attorney, Agent, or Firm* — Boyle Fredrickson, S.C.

(57) ABSTRACT

A molecule sequencer uses a planar nanochannel for aligning molecules to flow past impedance interrogation electrodes mounted across the channel for rapid sequencing. The electrodes may be fixed to the channel walls to provide improved registration by co-fabrication with the channel. Extended channel length over normally used nanopores can provide improved control of longer molecules and allow parallel sequencers to be readily fabricated on a single substrate.

19 Claims, 4 Drawing Sheets

PLANAR HIGH-SPEED MOLECULE SEQUENCER

STATEMENT REGARDING FEDERALLY SPONSORED RESEARCH OR DEVELOPMENT

- -

CROSS REFERENCE TO RELATED APPLICATION

- -

BACKGROUND OF THE INVENTION

The present invention relates to a system for the direct sequencing of long-chain molecules such as DNA and RNA and proteins by passing the molecules through a nanoscale channel and measuring an electrical signal modulated by the molecule passing through the pore.

Genetic information may be encoded in a molecule of deoxyribonucleic acid (DNA) as a sequence of nucleotides: guanine, adenine, thymine, and cytosine. Discovering the sequence of these nucleotides in DNA and other similar molecules is a foundational technology in biological studies.

One promising method of sequencing is "nanopore sequencing" in which a single strand of DNA, forming half of the DNA helix, is passed through a nanoscale opening in a membrane between two reservoirs. This nanopore opening may, for example, be a biological pore, a solid-state pore, a semiconductor pore (nanochannel) or a DNA synthesized channel held in a lipid bilayer. By a driving force, e.g., an electrical potential applied across the reservoirs, an ion flow is produced between the reservoirs pulling the strand of DNA through the nanopore. As the strand passes through the nanopore, it modulates the ion current through the nanopore as a function of the size of the nucleotide, which partially obstructs the nanopore. This fluctuation in the ion current may then be analyzed to determine the nucleotide sequence.

The electrical signals produced by changes in ion current through a nanopore with different nucleotides are very small in amplitude and, most importantly, short in time span. For this reason, it can be hard to obtain reliable measurements having sufficient resolution to distinguish between different molecules in the sequence. Critically the size of the nanopore must be small to ensure orderly passage of the aligned molecule through the nanopore and to accentuate changes in ionic current. Such small sizes may be obtained by using biological pore molecules or retro percussive techniques developed by the present inventors.

U.S. Pat. Nos. 9,086,401 and 9,488,600 assigned to the assignee of the present application and hereby incorporated by reference, describe methods of analyzing the operation of nanopore ion channels using changes in impedance across a nanopore measured at radio frequencies. In these techniques the nanopore suspended in the membrane is flanked by conductor antennas that couple across the nanopore to measure changes in impedance (e.g., capacitance) caused by passage of the components of the molecule. This impedance measuring technique can provide gigahertz bandwidth representing a considerable advance in readout speed in comparison to techniques that measure ionic current or tunneling.

The necessarily small size of the nanopore suspended within a membrane can present significant challenges in positioning the antennas close to the nanopore in a stable fashion.

SUMMARY OF THE INVENTION

The present invention provides a molecular sequencing device having a planar topology in which the nanopores are replaced by nanochannels thereby eliminating the membrane and allowing the antennas to be fixed to the channel walls. Suitably narrow channels can be constructed using innovative nano-imprint lithography techniques. The ability to make nano-width channels of arbitrary length improves the ability to sequence long molecules, and the planar structure simplifies construction of parallel sequencers on a single substrate. Concurrent construction of the antennas and nano channels can provide precise registration of these two elements for high-quality coupling. In addition, a planar structure allows the construction of novel serpentine channels to provide improved fluid control and present opportunities for redundant or sequential measurements.

More specifically, in one embodiment, the invention provides a molecule sequencing system having a substrate extending along a plane and supporting at least one analysis cell. The analysis cell may comprise: (a) a nanometer-width nanochannel in the substrate extending along a plane between an entrance and exit point of the nanochannel; and (b) a first and second conductive electrode each fixed relative to the nanochannel in flanking opposition across a width of the nanochannel between the entrance and exit point of the nanochannel. Measurement circuitry may apply a radiofrequency signal across the first and second conductive electrode to measure a change in the radiofrequency signal with the passage of a molecule through the nanochannel between the first and second conductive electrode.

It is thus a feature of at least one embodiment of the invention to provide a planar structure providing improved high-speed impedance measurement and permitting more sophisticated topologies and parallel channel formation using readily available manufacturing techniques.

The nanochannel may have a width less than 100 nanometers or in some embodiments a width less than 50 nanometers.

It is thus a feature of at least one embodiment of the invention to provide channel dimensions comparable to nanopore structures successfully used in the prior art.

The channel may have a length greater than 50 times its width.

It is thus a feature of at least one embodiment of the invention to provide longer constraining regions for visualizing and measuring long molecules and/or providing improved stability and/or offering the opportunity for additional analysis through multiple sensors distributed along the channel.

At least one of the entrance and exit points of the nanochannel may communicate between the nanochannel and a larger reservoir by means of a tapered transition structure.

It is thus a feature of at least one embodiment of the invention to provide improved coupling of the nanochannels with a larger reservoir reducing shear forces and turbulence that could damage or distort the molecules.

The tapered structure may decrease in width in two dimensions as liquid moves toward the nanochannel.

It is thus a feature of at least one embodiment of the invention to provide a multidimensional flow gradient that may improve centering and location of the molecules of interest.

The nanochannel may extend between the entrance and exit point in a serpentine path.

It is thus a feature of at least one embodiment of the invention to provide a long nanochannel to permit orientation an extension of the macromolecules before analysis in constrained dimensions of the substrate.

The first and second electrodes may be supported directly on the substrate.

It is thus a feature of at least one embodiment of the invention to provide highly accurate location of the electrodes with respect to the channel possible by fabricating both of these structures on the same substrate.

The first and second electrodes may taper inward toward each other to points proximate to the channel.

It is thus a feature of at least one embodiment of the invention to promote high-resolution measurements along the channel.

The substrate may define multiple analysis cells and include a first reservoir communicating with each entrance point of each analysis cell for parallel processing of a sample material passing from the first reservoir through each of the analysis cells.

It is thus a feature of at least one embodiment of the invention to permit high-speed parallel analysis of molecules in liquid suspension through multiple nanochannels.

The molecule sequencing system may provide a first reservoir communicating with an entrance point of the nanochannel and a second reservoir communicating with the exit point of the nanochannel wherein the first and second reservoirs each include electrodes for the application of a bias current across the nanochannel.

It is thus a feature of at least one embodiment of the invention to permit electrical "pumping" of molecules through the nanochannel, for example, using ionic flow.

The measurement circuitry may measure changes in impedance with the passage of a molecule between the first and second conductive electrode, for example, measuring changes in capacitance.

It is thus a feature of at least one embodiment of the invention to provide extremely high-speed sequencing possible using impedance measurements at gigahertz frequencies.

The substrate may provide a semiconductor material and the measurement circuitry may be constructed in the substrate using integrated circuit techniques.

It is thus a feature of at least one embodiment of the invention to permit extremely short conductor lengths between the antennas and processing circuitry to reduce noise and excess inductance and capacitance that would reduce the sensitivity of the measurement.

The conductive electrodes may be attached across an upper opening of the channel and the channel may undercut the conductive electrodes.

It is thus a feature of at least one embodiment of the invention to provide a channel cross-section that improves flow of the molecules in proximity to the electrodes.

The molecule sequencing system may further include at least one second sensor positioned adjacent to the channel providing a second measurement of a molecule passing through the channel with respect to a first measurement performed by the first and second conductive electrodes. The second sensor may provide third and fourth conductive electrodes fixed relative to the channel in flanking opposition across a width of the nanochannel between the entrance and exit point but displaced from the first and second conductive electrodes, and the measurement circuitry may apply a radiofrequency signal across the third and fourth conductive electrodes to measure change in the radiofrequency signal with the passage of the molecule between the first and second conductive electrodes and combine that measurement with the measurement performed by the first and second conductive electrodes.

It is thus a feature of at least one embodiment of the invention to permit multiple sequential measurements possible with extended nanochannel.

These particular features and advantages may apply to only some embodiments falling within the claims and thus do not define the scope of the invention.

DETAILED DESCRIPTION OF THE PREFERRED EMBODIMENT

Figure 1:
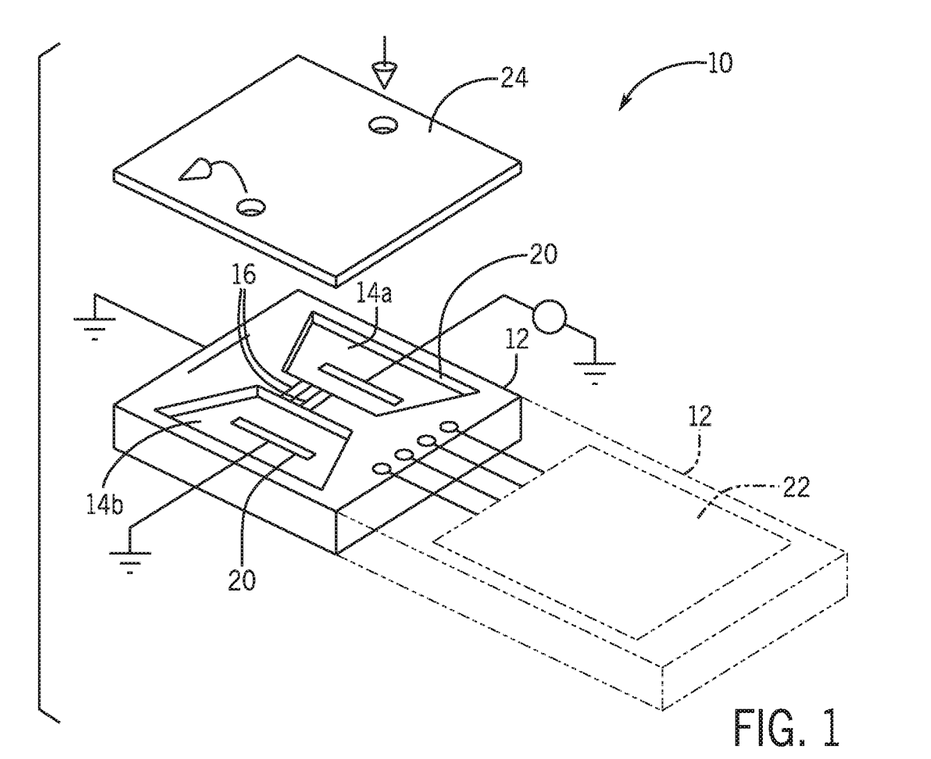
FIG. 1 is a simplified exploded perspective view of a nanochannel sensor of the present invention providing multiple nanochannels extending between reservoirs on a substrate.

Referring now to FIG. 1, a nanochannel sequencer 10 may provide for a substrate 12 having a first and second reservoir 14a and 14b formed in the upper surface thereof. The reservoirs 14a and 14b may hold, for example, a fluid such as a solution in which molecules to be analyzed are suspended. A set of nanochannels 16 may pass in parallel between the first reservoir 14a and the second reservoir 14b to conduct a flow of electrolyte and molecules to be analyzed between the reservoirs 14. That flow may be produced by a pressure difference, a sample concentration difference, or an electrical bias current, the latter, for example, causing ionic flow resulting from a voltage applied on a first reservoir electrode 20a in the first reservoir 14a with respect to a second reservoir electrode 20b in the second reservoir 14b. The nanochannels 16 are constructed, as will be discussed below, to promote the passing of a single strand of a biomolecule such as DNA, RNA, peptides, proteins, or the like axially aligned along the axis of the nanochannel 16.

Sensors (not shown in FIG. 1) associated with each of the nanochannels 16 may analyze the molecules passing through the nanochannels 16, for example, to sequence the molecule components, and may communicate with analysis circuitry 22 either off of the substrate 12 or integrated into the substrate 12 as will be discussed below. A cover 24 may be applied against the upper surface of the substrate 12 to cover the reservoirs 14a and 14b and to form a top surface of the nanochannels 16. Generally, the substrate 12 may also support multiple conductors, for example, applied on or beneath the surface of the substrate 12 to communicate between the sensors and the analysis circuitry 22 using integrated circuit techniques as will be discussed below.

The substrate 12 may be, for example, a semiconductor material such as silicon or other material suitable for fabrication of the structures to be described including integrated circuitry for circuitry 22. When circuitry 22 is not incorporated on the substrate 12, other substrate materials such as glass or polymer materials may be used. The cover 24, for example, may be transparent or silicate glass, for example, to promote easy visibility of the reservoirs 14a and 14b and to permit optical analysis of materials in the nanochannel 16 as may be desired.

Figure 2:
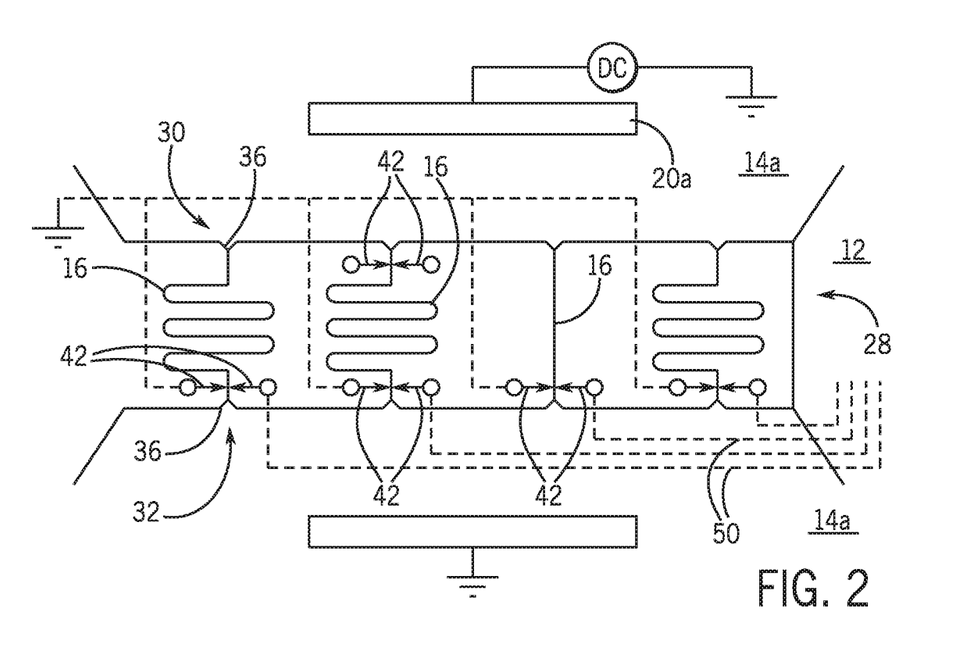
FIG. 2 is a top plan view of the nanochannels of FIG. 1 showing a possible serpentine configuration and the location of sensing electrodes.

Referring now to FIG. 2, multiple nanochannels 16 may be formed in an isthmus 28 separating the reservoir 14a from reservoir 14b and may extend generally along the plane defining the upper surface of the substrate 12. Each nanochannel 16 may connect to the entrance reservoir 14a at inlet 30 providing a tapered opening 36 leading from macroscopic entrance channels and narrowing as it connects to the nanochannel 16. The length of the nanochannel 16 may be serpentine to promote an extended period of laminar flow for improved handling of long molecules and to control their speed. Alternatively or in addition, some nanochannels 16 may be straight, the variation in shapes of the nano channel 16 allowing optimization for different molecule types or allowing measurements at different speeds such as may yield improved information. The remaining end of the nanochannel 16 communicates with an outlet 32 through a second tapered opening 36 expanding to reservoir 14b. The multiple nanochannels 16 may be displaced laterally across the isthmus 28 perpendicular generally to an axis extending between the inlet 30 and outlet 32 of each nanochannel 16.

Figure 3:
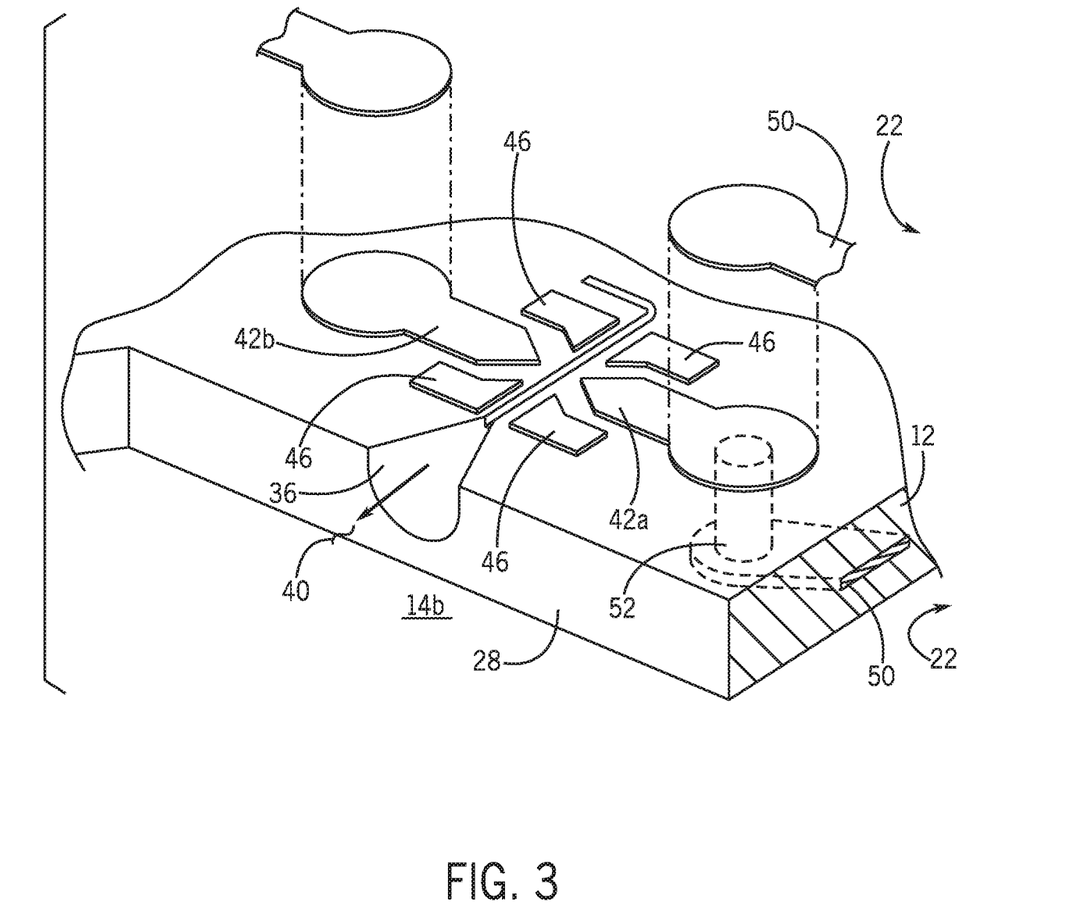
FIG. 3 is a fragmentary perspective view of one end of the nanochannel showing a funnel-shaped transition to the nanochannel, ground plane electrodes flanking the sensing electrodes, and conductive pathways between the sensing electrodes and measurement circuitry.

Referring now to FIGS. 2 and 3, as noted, each nanochannel 16 may join with the reservoirs 14 by means of a tapered opening 36 expanding smoothly in two dimensions of height and width with from the cross-sectional area of the nanochannel 16 to a larger cross-sectional area joining with the reservoir 14. This tapered opening 36 promotes smooth flow between the entrance reservoir 14a and the nanochannel 16 without excessive sheer force or folding of the molecules passing therethrough and being analyzed.

Positioned on opposite sides of the nanochannel 16 near the outlet 32 are analyzing electrodes 42a and 42b allowing electrical analysis of the molecules 40 flowing through the channel between the electrodes 42. Generally, the electrodes may taper to a point centered on or at the edge of the nanochannel 16 to provide maximum conductive area up to the nanochannel 16 but then focusing the measurement of the electrodes 42 to a very small region associated with a molecular component such as an RNA base pair. The present invention can provide precise placement of the electrodes 42 with respect to the channel by means of co-fabrication of these structures providing automatic registration to be described below. As a result, extremely close spacing of the electrodes 42a and 42b at the small scales of the channel of approximately 30 nanometers width can be obtained. In this regard, the width of the nanochannel 16 may be less than 500 nanometers wide and preferably less than 100 nanometers wide.

The electrodes 42a and 42b form a planar microstrip having waveguide characteristics when flanked by ground planes 46 (shown in fragment in FIG. 3) to provide a metallic micro-strip optimized for the desired frequency of measurement. Details on the construction of such microstrips are provided in the cited U.S. Pat. No. 9,086,401 incorporated by reference.

In some embodiments, duplicated flanking electrodes 42 may be formed at one or more different locations along a length of the nanochannel 16. By providing multiple sensing locations, redundant measurements may be made to reduce errors and allow higher-speed processing. Similarly, other sensor types may be incorporated along the nanochannel 16 including, for example, optical sensors, tunneling sensors, and the like. Example optical sensors include, for example, a nano-plasmonic antenna placed in the center of a nanochannel per Di Fabrizio et al., Journal of Optics 18, 063003 (2016)] or related approaches described in P. Gwozdz et al., Appl. Phys. Lett. 109, 223103 (2016); https://doi.org/10.1063/1.4970788 hereby incorporated by reference.

Each of the electrodes 42 may connect to traces 50 leading to the analysis circuitry 22. In one embodiment, the traces 50 may connect through the use of conductive vias extending downwardly into the substrate 12 to buried traces 50 that may pass beneath the nanochannels 16 and constructed using techniques understood in the field of integrated circuit design. In an alternative embodiment, the cover 24 may include cover traces 50 that may attach to pads associate with each of the electrodes 42 (capacitively or through a conductive adhesive or the like) to provide an alternative conduction path also free from interference with the nanochannel 16. Generally, one of the antennas, for example, 42b may be grounded and the other of the electrodes 42a may be received by analysis circuitry 22.

It will be appreciated that the circuitry 22 may in fact be incorporated into the substrate 12 immediately adjacent to the electrodes 42 to provide reduced signal loss and impedance such as may affect the frequency of operation, noise, or the like.

Referring now to FIGS. 4a-k, fabrication of the nanochannel sequencer 10 may make use of ultraviolet nano imprint lithography capable of producing the extremely small structures required and free from the limitations of standard optical techniques. In a first step, a conductor stamp 60 may be constructed having downwardly extending ridges 61 following the layout of the electrodes 42 and ground planes 46 to be applied to the substrate 12. For example, the conductor stamp 60 may be a hard silicon etched by focused ion beams, for example, using a Zeiss Crossbeam 550 ion beam scanning electron microscope.

Figure 4A:
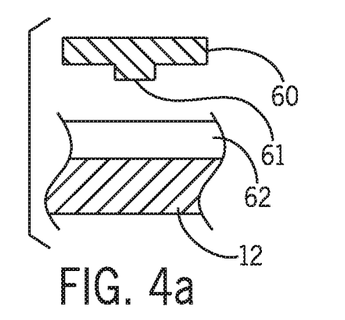
FIGS. 4a-h are simplified elevational cross-sections showing steps of the manufacturing processes for producing the nanochannels and electrodes of the present invention.

The substrate 12 may then be prepared by coating it with a resist layer 62, for example, by spin coating. In one embodiment, the resist layer 62 may be an ultraviolet curable hybrid polymer, for example, a polymer sold by Micro-Resists Technology of Germany under the tradename Ormostamp. Prior to this time, the substrate 12 may have been prepared to incorporate any buried traces 50 positioned in the correct locations and/or may include integrated circuitry prepared by normal integrated circuit technologies for implementing all or part of the analysis circuitry 22, These same standard integrated circuit techniques may be used to prepare the micro-structures of the reservoirs 14 prior to adding the resist layer 62.

Figure 4B:
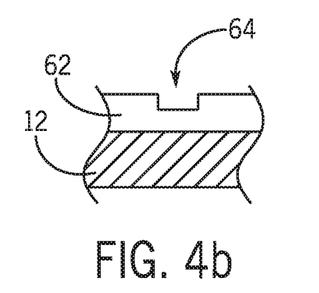

The stamp 60 is then pressed into the resist layer 62 and hardened using ultraviolet light to leave an impression 64 associated with each of the metallic conductors as shown in FIG. 4b when the stamp 60 is removed.

Figure 4C:
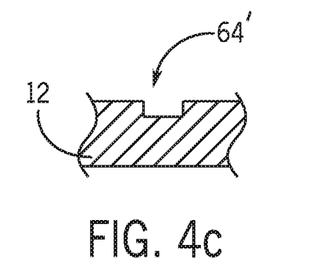

Referring to FIG. 4c, reactive ion etching may be used to etch away the resist layer 62 with the effect of producing an impression 64' in the upper surface of the substrate 12 corresponding to the impression 64 in the resist layer 62 and resulting from the faster ion etching in the region of the impression 64.

Figure 4D:
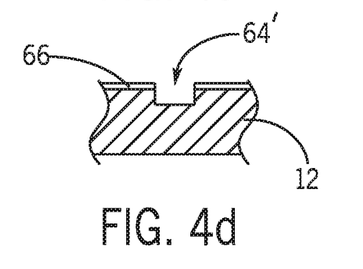
Figure 4E:
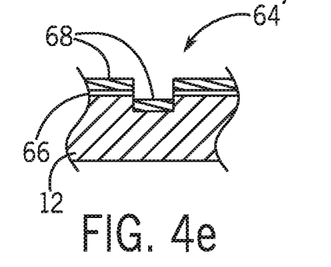

Referring to FIG. 4d, a shadow evaporation of a sacrificial or release layer 66 may then be performed to provide a coating over the upper surface of the substrate 12 outside of the impression 64'. In one embodiment, the release layer may be chromium. The application of the layer 66 can be followed, as shown in FIG. 4e, by an evaporation of gold to form a gold layer 68 which coats the upper surface of the release layer 66 and fills the impression 64'.

Selective etching or adhesive removal of the release layer 66 provides a remaining gold layer 68 that can form the electrodes 42 and ground planes 46 discussed above.

Figure 4F:
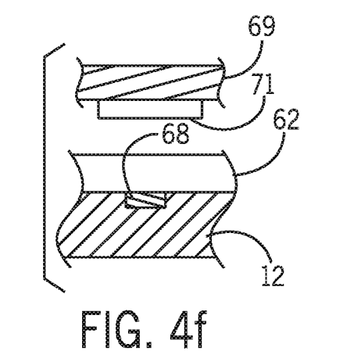
Figure 4G:
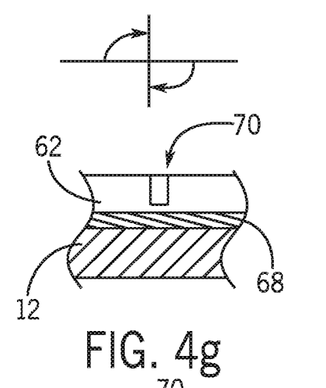

At this point a second stamp 69 may be prepared having downward projections 71 describing the nanochannels 16 and the tapered openings 36 using techniques similar to those used with stamp 60. The upper surface of the substrate 12 is again coated with resist layer 62, and as shown in FIG. 4g, the second stamp 69 is pressed into the resist layer 62 to leave an impression 70 associated with the nanochannel 16 and tapered opening 36.

Figure 4H:
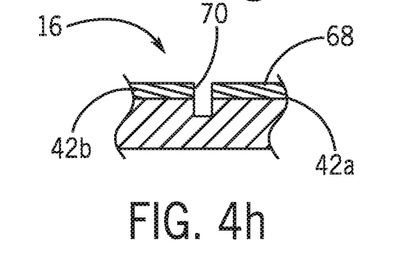

Referring now to FIG. 4h, further reactive ion etching removes the remaining resist layer 62 and forms a channel 70' corresponding to impression 70 that provides the nanochannel 16 and cuts through the gold layer 68 providing perfect registration between the edges of the electrodes 42 and the resulting nanochannel 16.

Figure 5:
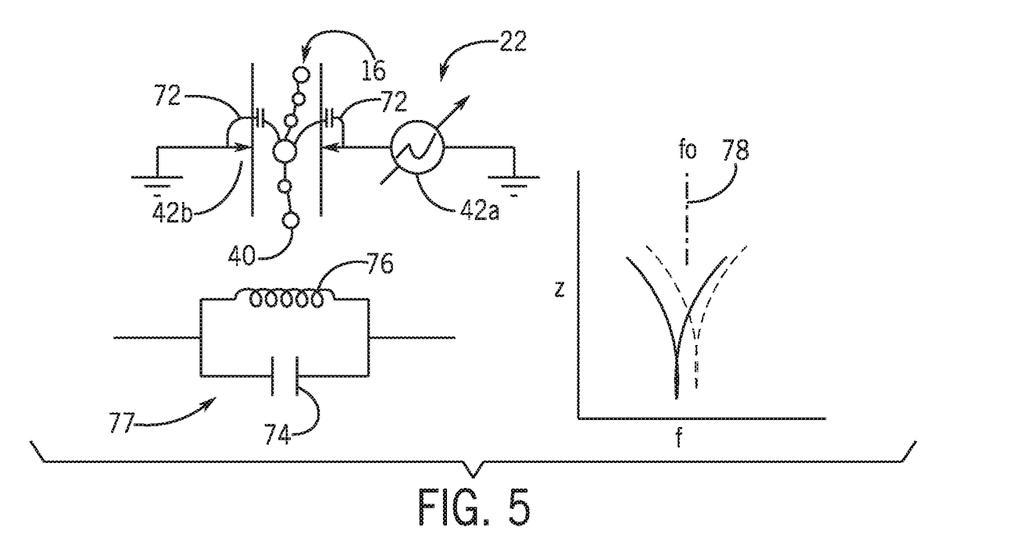
FIG. 5 is a schematic mechanical and electrical diagram illustrating operation of the nanochannels and the flanking electrodes in measuring molecule components and a graph showing measurement of impedance changes.

Referring now to FIGS. 1 and 5, the measurement circuitry 22 may apply a high-frequency signal across the electrodes 42a and 42b which experience capacitive coupling 72 with components of the molecule 40 passing between the electrodes 42. This capacitive coupling 72 may be part of a distributed capacitance 74 working with the distributed inductance 76 of the conductors and the electrodes 42 to form a tank circuit 77 having a natural resonant frequency 78 determined by the values of the capacitance 74 and inductance 76. Changes in the capacitance caused by movement of the molecule 40 between the electrodes 42 changes the center frequency 78 of this tank circuit 77 which can be measured to provide a corresponding measurement of the molecular components for sequencing. The analysis circuitry 22 may apply a frequency matching of the natural resonance of the system in the range of 0.1-10 GHz, thus being orders of magnitude higher than existing DC recordings that are limited in bandwidth to 1-MHz. This translates into a sequencing speed of the up to 0.1 nsec/base pair. Additional detail on this measurement technique is described in the above cited patent applications and other references incorporated into this application including, in particular, "A tank-circuit for ultrafast single particle detection in micropores" cited below.

Generally, extremely close proximity of the electrodes 42 to the molecule 40 provided by the present invention provides high sensitivity to changes in capacitance and improved resolution in the sequencing process.

The circuitry 22 may include a processor or the like executing a program for analyzing the signals including, for example, combining the signals of multiple sensors using averaging or the like or other statistical techniques. In some embodiments, the circuitry 22 may be divided between the substrate 12 and locations off of the substrate 12 and circuitry on the substrate 12 serving to boost the signal received for remote transmission.

Figure 6:
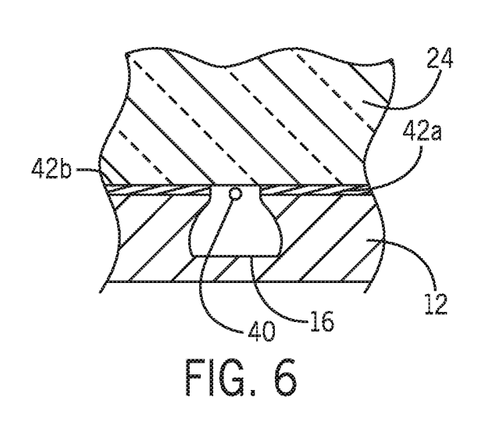
FIG. 6 is an elevational cross-sectional view through the nanochannel when covered with a cover showing the undercutting which serves to help align the molecule being analyzed.

Referring now to FIG. 6, generally the nanochannel 16 in the substrate 12 will be covered, for example, with a cover 24 shielding it from contamination and evaporation of the carrier fluid for the molecule 40. The cover 24 may have a thin conductive layer, e.g., single or double layer graphene, permitting a passage of a current across the gap between the electrodes 42 considerably larger than the typical tunneling current providing a faster signal read out and a better signal-to-noise ratio.

Figure 7:
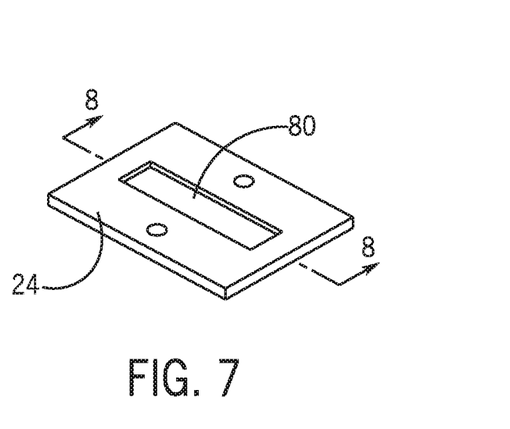
FIG. 7 is a perspective view of an alternative design of the cover of FIG. 1 having a thinned region over the nanochannels providing improved visibility and measurement of the molecules passing therethrough by optical means.
Figure 8:
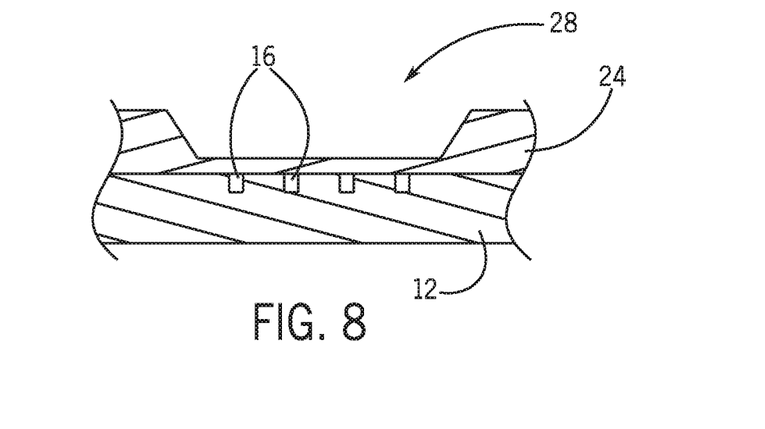
FIG. 8 is a cross-section along line 8-8 of FIG. 7 showing the thinned region.

Referring now to FIGS. 7 and 8, the cover 24 may have a thinned region 80 framed by thicker supporting material so that the thinned region 80 may fit over the isthmus 28 holding the nanochannels 16 for improved accessibility for light measurement simulation and the like, for example, using an inverted microscope, a UV-fluorescent lamp and an ultra-high sensitivity CCD camera. This thinned region 80 may be as thin as 20 nanometers and may be coated on its underside with single or multiple layer graphene or other conductor for electrical shielding while providing light transmission. The cover may be constructed of other materials including, for example, a silicon nitride ($Si_3N_4$) wafer and may be bonded to the substrate 12.

The nanochannel 16 will slightly undercut the electrodes 42 providing a cross-section that is believed to assist in centering and alignment of the molecule 40 therein.

The following documents describe previous work by the inventors and are hereby incorporated by reference:

Abhishek Bhat, Paul V. Gwozdz, Arjun Seshadri, Marcel Hoeft, and Robert H. Blick, A tank-circuit for ultrafast single particle detection in micropores, arXiv:1711.01126 (2017);

Radio Frequency Tank Circuit for Probing Planar Lipid Bilayer Formation', A. Bhat, H. Qin, J. Rodriguez, H. C. Shin, H. Shin, D. Kreft, J. Park, E. Stava, M. Yu, and, R. H. Blick, Soft Nanoscience Letters 3, 87-92 (2013); DOI: 10.4236/snl.2013.34016;

'Rapid fabrication and piezoelectric tuning of micro- and nanopores in single crystal quartz', Eric Stava, Minrui Yu, Hyun Cheol Shin, Hyuncheol Shin, Dustin Kreft, and Robert H. Blick, Lab Chip 13, 156-160 (2013); DOI: 10.1039/C2LC40925A. http://pubs.rsc.org/ doi: 10.1039/C2LC40925A;

'Mechanical actuation of ion channels using a piezoelectric planar patch clamp system', E, Stava, M. Yu, H. C. Shin, H. Shin, J. Rodriguez, and R. H. Buick, Lab Chip 12, 80-87 (2012), DOT: 10.1039/C1LC20636B; Advance Article—inside cover title (http://pubs.rsc.org/en/content/articlelanding/2012/1c/c11c90128a); DOI: 10.1039/C1LC90128A;

'Radio Frequency Response of Single Pores and Channels', H. S. Kim, S. Ramachandran, E. Stava, D. W. van der Weide, and R. H. Blick, New journal of Physics 13, 093033 (2011); http://iopscience.iop.org/1367-2630/13/9/093033/; DOI: 10.1088/1367-2630/13/9/093033;

'Direct Microwave Transmission Measurement on Single α-HL pores', S. Ramachandran, D. W. van der Weide, and R. H. Blick, Applied Physics Letters 99, 093105 (2011); DOI.org/10.1063/1.3626586.

Certain terminology is used herein for purposes of reference only, and thus is not intended to be limiting. For example, terms such as "upper," "lower," "above," and "below" refer to directions in the drawings to which reference is made. Terms such as "front," "back," "rear," "bottom," "side," "left" and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second" and other such numerical terms referring to structures do not imply a sequence or order unless clearly indicated by the context.

When introducing elements or features of the present disclosure and the exemplary embodiments, the articles "a," "an," "the" and "said" are intended to mean that there are one or more of such elements or features. The terms "comprising," "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

All of the publications described herein including patents and non-patent publications are hereby incorporated herein by reference in their entireties.

We claim:

1. A molecule sequencing system comprising:
   a substrate extending along a plane and supporting at least one analysis cell comprising:
   (a) a nanometer-width nanochannel in the substrate, the nanochannel extending along a first axis in a plane between an entrance point and exit point of the nanochannel;
   (b) a first and second conductive electrode each positioned relative to the nanochannel in flanking opposition along a second axis perpendicular to the first axis and separated across a width of the nanochannel between the entrance and exit point of the nanochannel; and
   measurement circuitry applying a radiofrequency signal across the first and second conductive electrodes to measure a change in the radiofrequency signal with a passage of a molecule through the nanochannel between the first and second conductive electrodes;
   wherein the channel has a length greater than 50 times its width.

2. The molecule sequencing system of claim 1 wherein the nanochannel has a width less than 100 nanometers.

3. The molecule sequencing system of claim 2 wherein the nanochannel has a width less than 50 nanometers.

4. The molecule sequencing system of claim 1 wherein at least one of the entrance and exit points of the nanochannel communicates between the nanochannel and a larger reservoir through a tapered transition structure.

5. The molecule sequencing system of claim 4 wherein the tapered structure decreases in width in two dimensions as liquid moves toward the nanochannel.

6. The molecule sequencing system of claim 1 wherein the nanochannel extends between the entrance and exit point in a serpentine path.

7. The molecule sequencing system of claim 1 providing multiple nanochannels extending between entrance and exit points wherein a length and/or curvature of the nanochannels differs.

8. The molecule sequencing system of claim 1 wherein the first and second electrodes are supported on the substrate.

9. The molecule sequencing system of claim 1 wherein the first and second electrodes taper inward toward each other to points proximate to the nanochannel.

10. The molecule sequencing system of claim 1 wherein the substrate defines multiple analysis cells and includes a first reservoir communicating with each entrance point of each analysis cell for parallel processing of a sample material passing from the first reservoir through each of the analysis cells.

11. The molecule sequencing system of claim 1 further including a first reservoir communicating with the entrance point of the nanochannel and a second reservoir communicating with the exit point of the nanochannel wherein the first and second reservoirs each include electrodes for application of a bias current across the nanochannel.

12. The molecule sequencing system of claim 1 wherein the measurement circuitry measures changes in impedance with the passage of a molecule between the first and second conductive electrode.

13. The molecule sequencing system of claim 12 wherein the measurement circuitry measures a change in capacitance between the first and second conductive electrodes.

14. The molecule sequencing system of claim 1 wherein the substrate provides a semiconductor material and the measurement circuitry is constructed in the substrate using integrated circuit techniques.

15. The molecule sequencing system of claim 1 wherein the first and second electrodes are attached across an upper opening of the channel and the channel undercuts the electrodes.

16. The molecule sequencing system of claim 1 further including at least one second sensor positioned adjacent to the channel providing a second measurement of a molecule passing through the channel with respect to a first measurement performed by the first and second conductive electrodes.

17. The molecule sequencing system of claim 16 wherein the second sensor is a third and fourth conductive electrodes fixed relative to the channel in flanking opposition across a width of the nanochannel between the entrance and exit point but displaced from the first and second conductive electrodes, and wherein the measurement circuitry applies a radiofrequency signal across the third and fourth conductive electrodes to measure change in the radiofrequency signal with the passage of the molecule between the first and second conductive electrodes and combines that measurement with the measurement performed by the first and second conductive electrodes.

18. The molecule sequencing system of claim 1 wherein the nanochannel is covered with a transparent and/or conductive material.

19. A method of sequencing a molecule sequencing system using
   a substrate extending along a plane and supporting at least one analysis cell comprising:
   (a) a nanometer-width nanochannel in the substrate, the nanochannel extending along a first axis in a plane between an entrance and exit point of the nanochannel;
   (b) a first and second conductive electrode each positioned relative to the nanochannel in flanking opposition along a second axis perpendicular to the first axis and separated across a width of the nanochannel between the entrance and exit point of the nanochannel; and
   measurement circuitry applying a radiofrequency signal across the first and second conductive electrodes to measure a change in the radiofrequency signal with a passage of a molecule through the nanochannel between the first and second conductive electrodes, the method comprising:

(a) pumping a liquid through the nanochannel containing molecules to be analyzed such that the nanochannels cause the molecules to axially align with the channels;
(b) during motion of the molecules between the first and second conductive electrodes, obtaining multiple measurements of change in radiofrequency signal; and
(c) correlating the changes in radiofrequency signal to molecule components;

wherein the channel has a length greater than 50 times its width.

* * * * *